United States Patent
Sussman

[19]

[11] Patent Number: 5,888,065
[45] Date of Patent: Mar. 30, 1999

[54] DENTAL IMPLANT HOLE GUIDE ARRANGEMENT

[76] Inventor: Harold I. Sussman, 64 Popham Rd., Scarsdale, N.Y. 10583

[21] Appl. No.: 126,244

[22] Filed: Jul. 30, 1998

[51] Int. Cl.⁶ ....................................................... A61C 3/02
[52] U.S. Cl. ................................................................ 433/76
[58] Field of Search ..................................... 433/75, 76, 72

[56] References Cited

U.S. PATENT DOCUMENTS

| | | | |
|---|---|---|---|
| 3,254,413 | 6/1966 | Suga | 433/76 |
| 3,380,163 | 4/1968 | Westerman | 433/76 |
| 4,344,755 | 8/1982 | Gold et al. | 433/76 |

*Primary Examiner*—Nicholas D. Lucchesi
*Attorney, Agent, or Firm*—Notaro & Michalos P.C.

[57] ABSTRACT

A dental implant guide arrangement is capable of accurately guiding a bur for drilling a pilot hole for a dental implant. The arrangement includes a pair of C-shaped jaws which engage lingual and buccal surfaces of a tooth and are held to each other by a fixing mechanism, such as a screw. A guide member extends from one of the jaws and has a semi-cylindrical guide that is parallel to an acceptable axis for the pilot hole. The bur can be guided along the guide for accurately drilling the pilot hole.

18 Claims, 5 Drawing Sheets

DENTAL IMPLANT HOLE GUIDE ARRANGEMENT

FIELD AND BACKGROUND OF THE INVENTION

The present invention relates in general to dental implants, and in particular to a new and useful dental implant hole guide arrangement which provides a dentist with an accurate guide to follow for drilling the critical initial pilot hole for a dental implant so that the hole is aligned on an acceptable axis in the patient's jaw bone, without endangering adjacent teeth.

Since 1981, dental root form implants have become a standard procedure for replacing missing teeth. Unlike other dental procedures such as crown and bridge work, root canals and the like, which utilize at least part of the original tooth as a foundation for the tooth replacement, implants require the drilling of holes directly into the bone of the jaw.

Although the dental implants have many benefits, particularly where a patient is missing teeth over large portions of the mouth, various complications can follow implant placement, especially to adjacent teeth. The bone may be overheated during implant surgery for example and this can devitalize an adjacent tooth. Endodontic lesions can also form which compromise the implant fixture by preventing integration of the bone around the fixture (Osseointegration) causing loss of the implant.

Another potentially more serious problem involves traumatic injury to the root of an adjacent tooth which is in the path of the hole drilled for the implant.

The case history of such a traumatic injury can be found in the inventor's article "Tooth Devitalization Via Implant Placement: A Case Report", Sussman, *Periodontal Clinical Investigations*, Vol. 20, No. 1, 1998, Northeastern Society of Periodontics, pp. 22–24.

FIG. 5 is a schematic diagram of an x-ray showing the cause of traumatic injury to a tooth 3 having a root 4 which was along the axis of a hole 5 drilled to receive an implant fixture 6. Tooth 3 was ultimately lost as was the implant 6 due to this traumatic injury.

Within the confines of the mouth, it is very difficult to accurately align a dental bur for drilling the crucial initial pilot hole of about 2 mm. in diameter. The pilot hole must be drilled along an acceptable axis into the jaw bone which both avoids any critical structures in the bone such as nerves, blood vessels and the like, but also avoids intersecting the root of an adjacent tooth which may not be apparent without x-rays. Even with x-rays, however, it is difficult for a dentist to accurately align the bur without some help.

One very complex and time consuming technique for properly aligning the initial implant hole for a patient is disclosed in U.S. Pat. No. 5,015,183 entitled LOCATING DEVICE AND METHOD OF PLACING A TOOTH IMPLANT. According to this method, a stent comprising a negative impression of a patient's teeth in the vicinity of the implant is taken. Multiple x-ray opaque strips are placed in the negative impression and an oblique x-ray is taken. This x-ray is used as a diagnostic tool for the patient's jaw structure to help plot the trajectory of an implant fixture in the jaw.

Once an acceptable initial implant hole is formed in the jaw, subsequent holes can be produced by using the initial hole as a guide. This is when multiple implants are to be installed. See, for example, U.S. Pat. No. 5,741,133 and U.S. Pat. No. 5,302,122. Other techniques and apparatuses for drilling holes in the jaw bone are disclosed in U.S. Pat. Nos. 4,787,848 and 4,998,881. A need remains, however, for a simple and effective tool which can be used particularly by general dentists to permit them to produce the initial pilot hole along an acceptable axis in a patient's jaw bone. Once the initial bore is made, it can be enlarged to the required final diameter, generally about 4 mm., using ever increasing bur sizes. Once the initial hole is drilled, the enlargements are easily made using the initial hole as the guide. The present invention provides a way of making that critical initial hole.

SUMMARY OF THE INVENTION

The present invention is used to drill a first, properly aligned pilot hole for an implant. It is conventional to drill an initial small diameter hole, about 2 mm., followed by enlarging the hole until the appropriate size for the implant is reached. This is done using different burs of ever increasing diameter until a final hole diameter of about 4 mm. is reached.

According to the present invention, a device having a guide to align the first pilot hole is provided. Guides are not necessary for the subsequent enlarging holes since the original pilot hole serves as a guide for drilling the subsequent holes.

The invention solves the serious prior art problem of improperly aligned implant holes which can actually endanger adjacent teeth.

Accordingly, an object of the present invention is to provide a dental implant hole guide arrangement for use in drilling a pilot hole for a dental implant which has an acceptable axis, the arrangement comprising tooth engagement means for engaging a tooth which is near the site in the patient's mouth for receiving the pilot hole, a fixing mechanism for fixing the engagement means to the tooth so that it does not move readily, and a guide member connected to the tooth engagement means and extending over the site, the guide member having a guide which is aligned with the acceptable axis of the pilot hole and which can be used to guide the movement of a dental bur for drilling the pilot hole.

Advantages of the invention include simplicity of construction with the preferred embodiment having only three parts. All parts of the invention are sterilizeable, particularly since no spring metal parts are needed. According to the present invention, the device is provided in four sizes, left and right bicuspid, and left and right molar. This insures that a preferred semi-cylindrical guide trough of the present invention, always faces the dentist, on the bucal side of the mouth. Other devices for other locations in the mouth are usually not necessary since the dentist can form the initial hole for the first implant without aides in the more accessible front areas of the mouth.

The guide device of the present invention provides four-point contact with the tooth surfaces to insure that the guide is orthogonal to the jaw bone and parallel to the adjacent tooth. This properly aligns the guide trough, giving the dentist a clear guide to follow for drilling the initial pilot hole. It is important to select a tooth which is an appropriate candidate for receiving the guide arrangement of the present invention. The tooth must have surfaces which can be accurately engaged by the arrangement, and a root structure which is parallel to these surfaces. The root must not curve toward the implant site and thus into the path of the pilot hole to be drilled. This avoids the prior art danger of inadvertently drilling into the root of an adjacent tooth.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
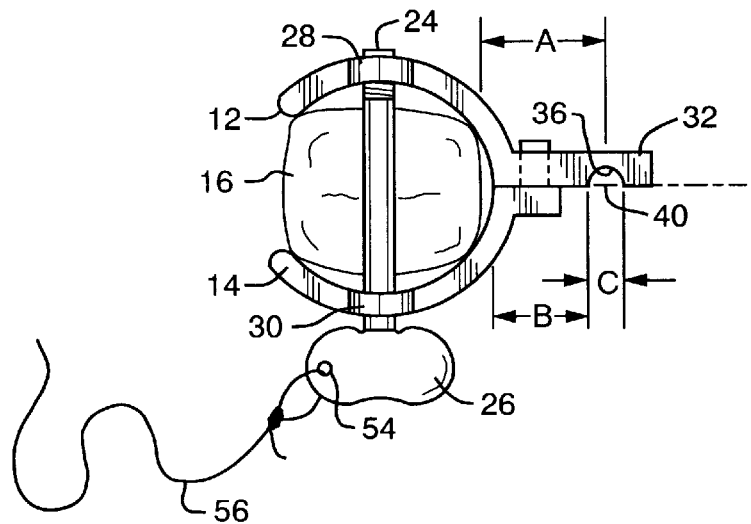
FIG. 1 is a top plan view of a first embodiment of the present invention shown engaged onto an appropriate candidate tooth serving as an anchor for the guide arrangement.

Referring to the drawings, the invention embodied therein is a new guide arrangement for guiding the formation of an initial pilot hole used to place a dental implant into the jaw bone of a patient.

Figure 5:
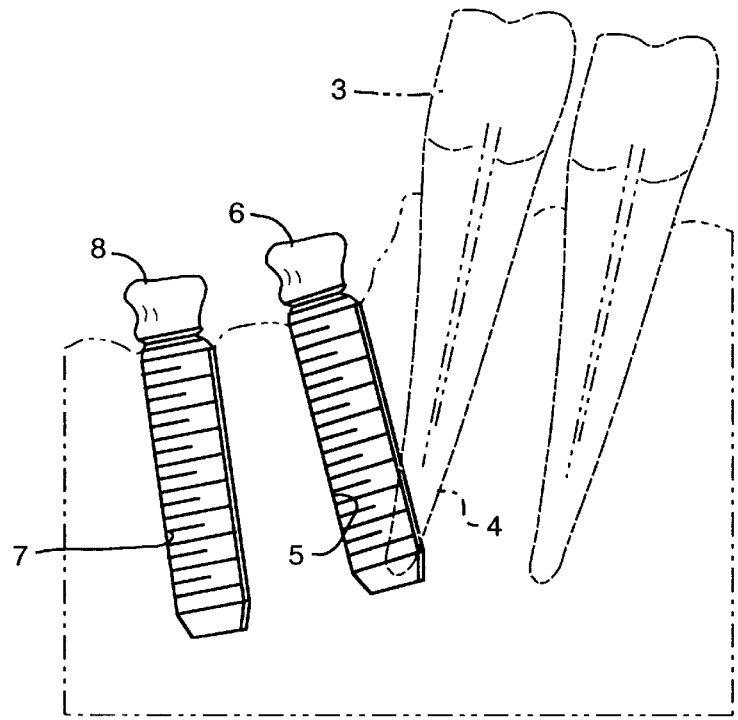
FIG. 5 is a schematic diagram illustrating an x-ray demonstrating prior art trauma to an adjacent tooth caused by an implant procedure.

Referring to FIGS. 1–4, the dental implant hole guide arrangement of the present invention comprises tooth engaging or clamp means in the form of a lingual jaw 12 and a buccal jaw 14 which are both arcuate and have an inner concave surface for embracing the respective lingual and buccal surfaces of an appropriate candidate tooth 16 which is adjacent the pilot hole 18 in a patient's jaw bone 20. According to the present invention, the candidate tooth 16 has one or more roots 22 which are not intersected by the pilot hole 18 or the large diameter implant hole to be eventually formed, such as hole 7 for implant 8 shown in FIG. 5.

According to the present invention, jaw attachment means are provided at the mesial end of each generally C-shaped jaw 12 and 14, which fix the relative position of the jaws at this end of the arrangement.

The opposite ends of the jaws are maintained at a spacing from each other even when the jaws are fixed on the tooth 16, for example, by a screw 24 having a wing nut type handle 26 for rotating the threaded part of the screw into a projection 28 containing a threaded hole and extending upwardly from the lingual jaw 12. A projection 30 extends upwardly from the buccal jaw 14 and contains an unthreaded hole which slidably receives the unthreaded shaft of screw 24, for free axial and rotational movement. In this way, by turning handle 26, the projections 28 and 30 can be squeezed toward each other, firmly embracing the tooth 16.

A guide member 32 is connected to, and extends mesially from the tooth engaging means in the form of jaws 12,14 over the implant site 34 which will receive the implant hole. Guide member 32 includes a guide 36 which, in the preferred embodiment of the invention, is a semi-cylindrical trough or recess defined in the buccal surface of guide member 32. Guide 36 extends parallel to an imaginary acceptable axis 40 for the implant pilot hole 18. Bur 42 shown attached to the head of a handpiece 44 must be carefully and accurately moved by the dentist down into the jaw along axis 40 to produce the properly positioned and aligned pilot hole 18.

The diameter of trough 36 shown at C in FIG. 1 is selected to be comparable to the diameter of the bur 42 to give the dentist an accurate guide to follow for drilling the pilot hole. As also shown in FIG. 1, the distance A between the mesial surface of tooth 16 and the axis 40 must be selected to properly center the implant hole for receiving its appropriate prosthetic tooth. More critical, the distance B between the mesial surface of the tooth 16 and the lateral edge of the implant hole must be no less than 2.5 mm. for bicuspids and 3.5 mm. for molars.

The sizes of the tooth engaging jaws 12,14 can also be provided to adapt typical bicuspid and molar teeth for adults and for left and right quadrants of the mouth. Accordingly, a set of guide arrangements of the present invention can be provided in practice to address each implant situation.

The mesial ends of the C-shaped jaws 12 and 14 in the embodiment of FIGS. 1–4, are fixedly connected to each other by a square tab 46 extending mesially from the mesial end of jaw 14, over a buccal surface of the guide member 32 which is not occupied by guide 36. This portion of guide member 32 contains a square or rectangular aperture 48 of a size to receive the head of a square hook 50 extending lingually from the lingual surface of tab 46. To connect the buccal jaw 14 to the lingual jaw 12, hook 50 is first inserted into aperture 48 until the head of the hook passes the lingual surface 52 of guide member 32. At this point, buccal jaw 14 is slid downwardly with respect to lingual jaw 12, aligning the upper and lower edges of the jaws as they appear in FIG. 4 and firmly engaging hook 50 onto guide member 32.

Handle 26 of screw 24 for the fixing means between the jaws is provided with a hole 54 which receives a loop of dental floss 56 which is tied through the hole 54 on the handle 26. This is to insure that the relatively small screw 24 is not lost in the patient's mouth and inadvertently swallowed or aspirated.

Figure 2:
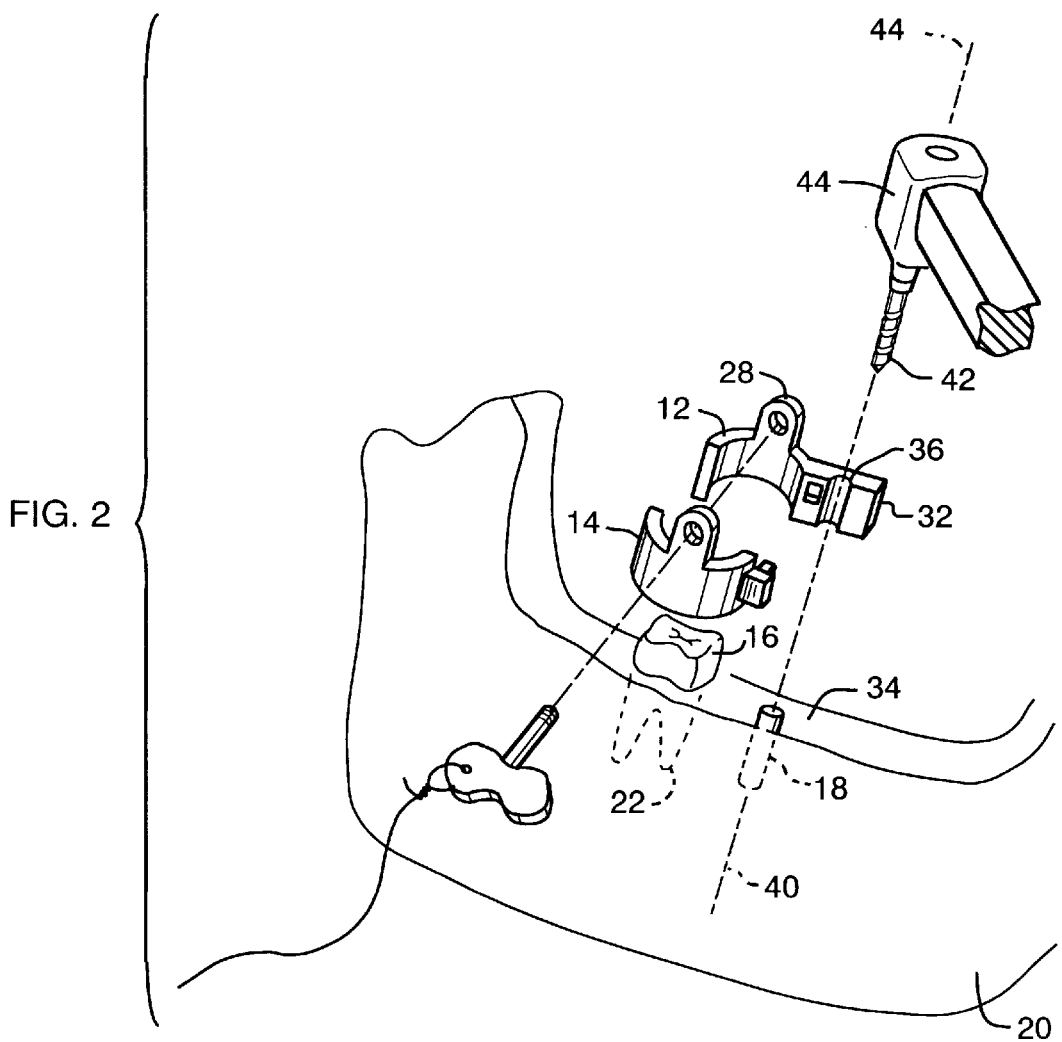
FIG. 2 is an exploded, schematic and perspective view of the invention showing the parts of its preferred embodiment in conjunction with a patient's jaw bone, a pilot hole to be drilled and a bur with part of a handpiece.
Figure 3:
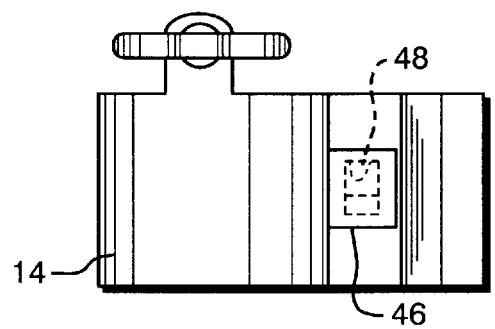
FIG. 3 is a side elevational view of the guide arrangement.
Figure 4:
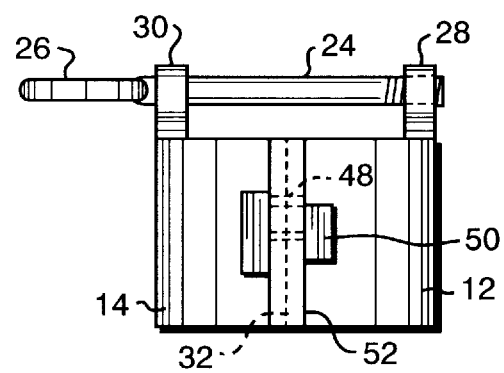
FIG. 4 is a mesial side elevational view of the embodiment of FIG. 1.

In the embodiment of FIGS. 1–2, the arrangement of the present invention is made up of only three parts (not counting the floss which is disposable), and can thus be made of surgical steel or other appropriate metal that can be sterilized repeatedly without degrading the metal. It is, of course, essential to sterilize the present invention, as is the case with all dental equipment meant for insertion into the mouth. This embodiment of the invention also avoids the use of any spring metal whose tempering and spring qualities will deteriorate if exposed to sterilization.

Figure 6:
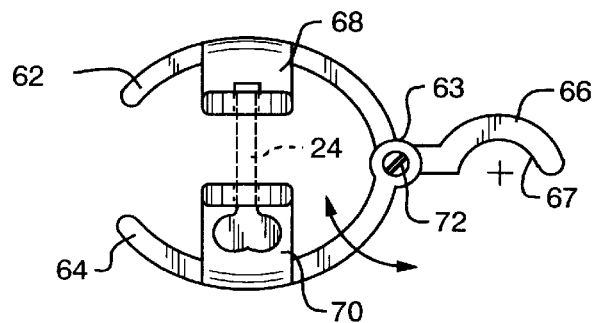
FIG. 6 is a top plan view of another embodiment of the invention.

FIG. 6 illustrates another embodiment of the invention which utilizes a lingual jaw 62 which is pivotally connected at a pivot hinge 63 to a buccal jaw 64. An S-shaped projection 68 extends upwardly from jaw 62 and a mirror projection 70 extends upwardly from jaw 64.

Figure 7:
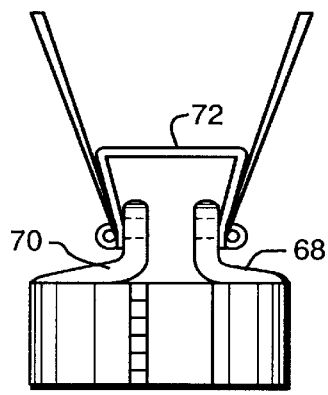
FIG. 7 is mesial side elevational view of the embodiment of FIG. 6 showing an alternate fixing means for holding the arrangement to a patient's tooth.

As shown in FIG. 7, a disposable spring clip 71 of conventional design can be used to bias the projections 68,70 toward each other and thus fix the engagement means to the tooth. In FIGS. 6 and 7, holes are shown through the upstanding portions of projections 68 and 70, one of which can be threaded and the other smooth for receiving a screw-type fixing mechanism 24 between the jaws. A threaded screw or pin 72 completes the hinge connection between the jaws. The hinge permits movement of the buccal jaw 74 in the direction of the curved arrow for engaging and disengaging a tooth. Guide member 66 having a guide 67 extends from the mesial end of either jaw 62 or jaw 64. Although workable, this embodiment utilizes the relatively small hinge pin 72 which must be disassembled for sterilization purposes and may be lost. Sterilization of the spring steel clip 72 is avoided by making that clip disposable.

Figure 8:
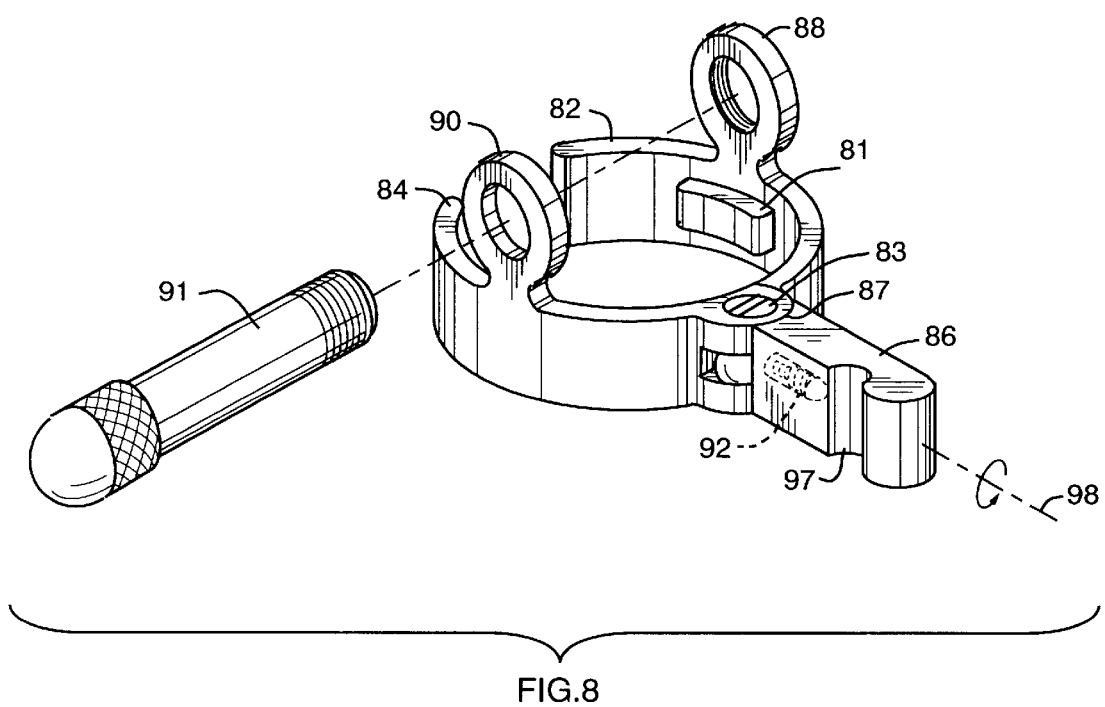
FIG. 8 is an exploded perspective view of a further embodiment of the invention.

FIG. 8 illustrates a still further embodiment of the invention having lingual and buccal jaws 82 and 84, respectively, with upwardly extending projections 88 and 90, projection 88 having a threaded hole and projection 90 having a smooth bored hole so that a fixing screw 91 can be used to hold the jaws together.

Hinge pin 83 completes a hinge between the mesial ends of jaws 82,84. A spring loaded pivot 92 is connected between the lingual jaw 82 and a guide member 86. The lateral end 87 of guide member 86 is curved to follow the contour of the outer surface of the hinge and, with the spring-loaded action of pivot 82, holds the guide member 86 with its guide 97 facing the dentist in the buccal direction. The device of FIG. 8 can be used also for an opposite side of the mouth, however, by rotating guide member 86 about axis 98 through the action of spring-loaded pivot 92. The curved lateral surface 87 holds the guide member 86 facing the buccal direction. FIG. 8 also illustrate another feature of the invention; namely, a stop pad 81 which is fixed on the inner surface of each of the jaws for engaging the lingual and buccal surfaces of the tooth to help better fix the arrangement to the tooth. In the preferred form of the invention, however, pads 81 are not provided.

Figure 9:
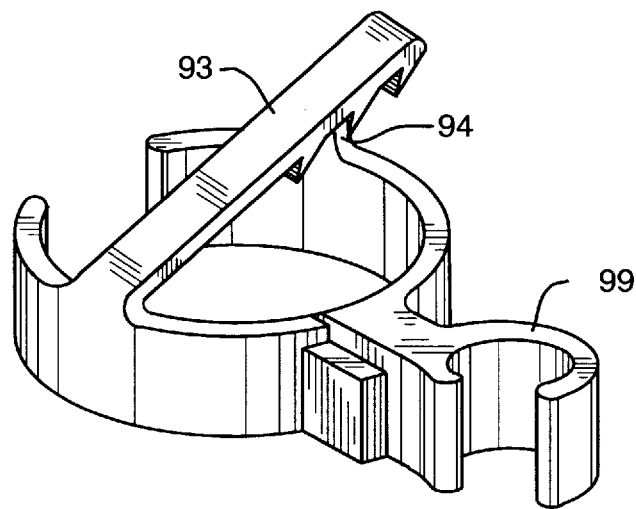
FIG. 9 is a perspective view of a still further embodiment of the invention.
Figure 10:
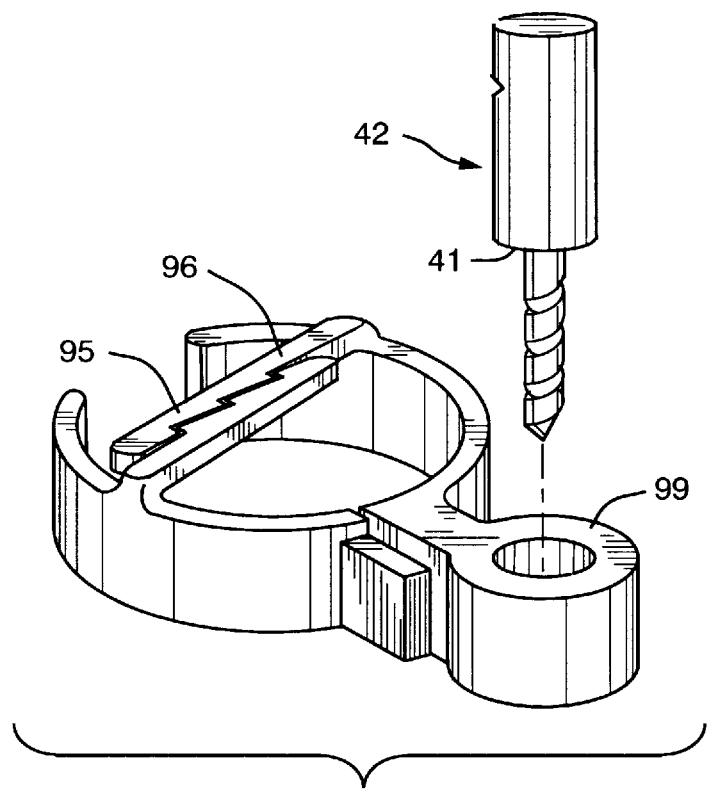
FIG. 10 is a perspective view of a still further embodiment of the invention.

FIG. 9 illustrates another fixing means of the present invention, this one in the form of a rack 93 having lower teeth, one of which engages a pinion tooth 94 extending upwardly from the other jaw. In FIG. 10, another toothed version of the holding means is in the form of a pair of toothed racks 95,96 which can engage each other to firmly hold the jaws against the opposite surfaces of the tooth. The use of flexible racks and teeth does not increase the complexity of the invention nor reduce the sterilizeability of the arrangement, but is somewhat more difficult to manipulate than the screw in the embodiment of FIG. 1.

Although arcuate, generally C-shaped, jaws are shown in the preferred embodiments of the invention, it is understood that the shape of the jaws can vary and in fact, a single jaw, loop or other structure can be used to engage the tooth. In addition, although the preferred form of the guide is a curved trough or recess, the guide can also be a hole through the guide member as shown in FIG. 10, and alternatively, a hole with a diameter (about 2.25 mm), slightly greater than the maximum bur diameter for a full guiding action (this is a 360° guide rather than the 180° guide of FIG. 1. Further, the fixing means which is preferably a screw can also be a spring-loaded clamp as shown in FIG. 7 or a rack and tooth arrangement as shown in FIGS. 9 and 10, or any other mechanism for holding the two parts of the engagement means against a candidate tooth adjacent the implant site.

FIG. 9 shows how a guide that extends about 270° around can be used. This allows the dentist to see the bur as it cuts and also to see the debris. White chips mean bone only is being cut. Blood or other debris may indiate a problem. Other guide circle portions may also be used, e.g., 150° to 330°. Also, the top side 99 of the guide member can serve as a stop for the large diameter shoulder 41 of a bur 42, to stop the downward movement and prevent too deep a hole. All of the embodiments of the injection can use the 360°, 180° or 270° degree guides as alternatives.

While specific embodiments of the invention have been shown and described in detail to illustrate the application of the principles of the invention, it will be understood that the invention may be embodied otherwise without departing from such principles.

What is claimed is:

1. A dental implant hole guide arrangement for use in drilling a pilot hole for a dental implant which has an acceptable axis, the arrangement comprising:
   tooth engagement means adapted to engage a tooth which is adjacent a site in a patients mouth for receiving the pilot hole for the dental implant, said tooth engagement means comprising a pair of arcuate jaws to be engaged to lingual and buccal surfaces of the tooth;
   fixing means connected to said engagement means for fixing said engagement means to the tooth; and
   a guide member connected to said tooth engagement means and adapted to extend over the site, said guide member having a guide which is aligned with the acceptable axis of the pilot hole to be drilled, said guide being shaped to guide a bur for drilling the pilot hole.

2. An arrangement according to claim 1, wherein said fixing means comprises a projection extending upwardly from each of the jaws and a fixing member connected between said projections.

3. An arrangement according to claim 2, wherein said fixing member comprises a screw.

4. An arrangement according to claim 3, wherein said screw includes a wing-nut head.

5. An arrangement according to claim 3, including a hole through the wing-nut head for receiving a string.

6. An arrangement according to claim 1, wherein said guide member is fixed to said tooth engagement means, said guide comprising a recess extending parallel to the acceptable axis.

7. An arrangement according to claim 6, wherein said recess is semi-cylindrical.

8. An arrangement according to claim 6, wherein the recess extends around a portion of a circle by about 150° to 330°.

9. An arrangement according to claim 6, wherein the guide recess is a closed circle.

10. An arrangement according to claim 6, wherein the guide member has a top surface that acts as a stop for stopping downward motion of a bur.

11. An arrangement according to claim 1, wherein said tooth engagement means, said fixing means and said guide member are all sterilizeable.

12. An arrangement according to claim 7, wherein said tooth engagement means comprises a pair of arcuate jaws having a mesial end connected to each other and an opposite lateral end which are spaced from each other when engaged to a tooth.

13. A dental implant hole guide arrangement for use in drilling a pilot hole for a dental implant which has an acceptable axis, the arrangement comprising:
   tooth engagement means adapted to engage a tooth which is adjacent a site in a patients mouth for receiving the pilot hole for the dental implant;

fixing means connected to said engagement means for fixing said engagement means to the tooth; and a guide member connected to said tooth engagement means and adapted to extend over the site, said guide member having a guide which is aligned with the acceptable axis of the pilot hole to be drilled, said guide being shaped to guide a bur for drilling the pilot hole;

said tooth engagement means, said fixing means and said guide member all being sterilizable, said tooth engagement means comprising a pair of arcuate jaws having a mesial end connected to each other and an opposite lateral end which are spaced from each other when engaged to a tooth.

14. An arrangement according to claim 13, including hook means for connecting the mesial ends of said jaws to each other.

15. An arrangement according to claim 14, wherein said guide member extends from a mesial end of a first one of said jaws, a tab extending from a second one of said jaws, one of said tab and guide member having a hole therein, and the other of said tab and guide member having a hook extending therefrom and engaged into said hole for connecting said jaws to each other.

16. An arrangement according to claim 15, wherein said fixing means comprises a projection extending upwardly from each of said jaws and a screw connected between said projections.

17. An arrangement according to claim 16, wherein said screw has a wing-nut handle.

18. An arrangement according to claim 15, wherein said guide comprises a recess in a surface of said guide member, said recess extending parallel to the acceptable axis.

* * * * *